(12) United States Patent
Sheldon et al.

(10) Patent No.: US 7,699,847 B2
(45) Date of Patent: Apr. 20, 2010

(54) GUIDE CLAMP FOR GUIDING PLACEMENT OF A GUIDE WIRE IN A FEMUR

(75) Inventors: Michael B. Sheldon, Cordova, TN (US); Ramon Luna, Memphis, TN (US); Steven F. Seyer, Germantown, TN (US); Brian Krehlik, Murfreesboro, TN (US)

(73) Assignee: Wright Medical Technology, Inc., Arlington, TN (US)

( * ) Notice: Subject to any disclaimer, the term of this patent is extended or adjusted under 35 U.S.C. 154(b) by 1071 days.

(21) Appl. No.: 10/994,110

(22) Filed: Nov. 19, 2004

(65) Prior Publication Data

US 2005/0113841 A1 May 26, 2005

Related U.S. Application Data

(60) Provisional application No. 60/523,799, filed on Nov. 20, 2003.

(51) Int. Cl.
*A61B 17/56* (2006.01)
(52) U.S. Cl. .............................. 606/53; 606/89; 606/96
(58) Field of Classification Search ............. 606/86–89, 606/96, 103–104; 408/105; 269/156, 234
See application file for complete search history.

(56) References Cited

U.S. PATENT DOCUMENTS

| 86,016 | A | | 1/1869 | Howell | |
|---|---|---|---|---|---|
| 887,103 | A | * | 5/1908 | Lane | 269/156 |
| 1,075,384 | A | * | 10/1913 | Siedel | 269/156 |
| 1,717,061 | A | | 9/1929 | Hicks | |
| 1,888,800 | A | * | 11/1932 | Grothe | 29/246 |
| 1,960,905 | A | * | 5/1934 | Graham | 408/83.5 |

(Continued)

FOREIGN PATENT DOCUMENTS

DE 1164019 2/1964

(Continued)

OTHER PUBLICATIONS

Beaule, et al. Jumbo Femoral Head for the Treatment of Recurrent Dislocation Following Total Hip Replacement. J Bone Joint Surg. 84A: 256-263 (2002).

(Continued)

*Primary Examiner*—Thomas C Barrett
*Assistant Examiner*—Nicholas Woodall
(74) *Attorney, Agent, or Firm*—Duane Morris LLP

(57) ABSTRACT

A guide clamp for clamping a femur and guiding placement of a guide wire relative to the femur. The guide clamp includes a body supporting a pair of clamping surfaces at the end of a pair of clamping arms that are spring-biased to move with respect to each other into a closed position to grip the femur. Defined by the body is a guide opening that guides insertion of the guide pin once the femur has been gripped. One of the clamping arms of the guide clamp may have proximal and distal portions that are slidably adjustable with respect to each other to allow a controlled repositioning of the guide opening with respect to the femur. The guide clamp may also include an engagement member which is supported by the body of the clamp and is capable of advancing into abutting contact with the head of the femur.

13 Claims, 12 Drawing Sheets

U.S. PATENT DOCUMENTS

| | | | |
|---|---|---|---|
| 2,416,228 A | 2/1947 | Sheppard | |
| 3,810,294 A * | 5/1974 | Link | 29/261 |
| 4,246,895 A * | 1/1981 | Rehder | 606/89 |
| 4,522,201 A | 6/1985 | Tongue | |
| 4,524,959 A * | 6/1985 | Kubo | 269/43 |
| 4,752,296 A | 6/1988 | Buechel et al. | |
| 4,896,663 A | 1/1990 | Vandewalls | |
| 4,976,740 A | 12/1990 | Kleiner | |
| 5,817,098 A * | 10/1998 | Albrektsson et al. | 606/96 |
| 5,997,582 A | 12/1999 | Weiss | |
| 6,156,069 A | 12/2000 | Amstutz | |
| 6,375,684 B1 | 4/2002 | Kriek | |
| 6,520,969 B2 | 2/2003 | Lambrecht et al. | |
| 6,595,999 B2 * | 7/2003 | Marchione et al. | 606/96 |
| 2005/0209597 A1 * | 9/2005 | Long et al. | 606/86 |
| 2005/0245936 A1 * | 11/2005 | Tuke et al. | 606/89 |

FOREIGN PATENT DOCUMENTS

| | | |
|---|---|---|
| DE | 10013331 A1 | 9/2001 |
| GB | 2372707 A | 9/2002 |
| JP | 0975366 | 3/1997 |
| WO | WO98/11837 A1 | 12/1989 |

OTHER PUBLICATIONS

Amstutz, et al. Range of Motion Studies for Total Hip Replacements. Clin. Orthop. Rel. Res. 111: 124-130 (1975).

International Search Report, PCT International Search Report mailed Mar. 25, 2003 for PCT/US2004/038931 filed Nov. 19, 2004.

* cited by examiner

GUIDE CLAMP FOR GUIDING PLACEMENT OF A GUIDE WIRE IN A FEMUR

CROSS REFERENCE TO RELATED APPLICATIONS

This application claims priority to Provisional Patent Application Ser. No. 60/523,799, filed Nov. 20, 2003, which is pending.

BACKGROUND OF THE INVENTION

1. Field of the Invention

The present invention is related to the use of guides for placement of guide wires in orthopedic surgery, and more particularly to the use of a guide clamp for placement of a guide wire during femoral head resurfacing surgery.

2. Description of Related Art

When severe hip joint problems are encountered, it is sometimes necessary to replace a portion of the hip joint; either the ball or the socket or both. One generally used hip joint replacement technique involved removal of a head and neck of the femur, and the insertion of a long angled and tapered metal prosthesis into the central "intramedulary" canal at the open upper end of the main straight portion of the femur. This femoral prosthesis typically had a relatively small metal ball at its upper end which mated with a small plastic socket mounted on the hip side of the joint. However, this "total" hip replacement technique was drastic, involving complete removal of the head and neck of the femur, and made any subsequent hip joint problems difficult to handle.

U.S. Pat. No. 4,123,806 to Amstutz, et al., discloses an early femoral prosthesis having a cobalt-chromium-molybdenum metallic shell of generally hemispherical shape. This femoral prosthesis is designed on the principle of removing all non-viable femoral head bone, but also preserving as much of the head and neck as possible.

In a more recent development, U.S. Pat. No. 6,156,069 to Amstutz ("the '069 patent"), which is commonly assigned and hereby incorporated herein by reference, discloses a metal-to-metal surface hip joint replacement. As shown in FIGS. 1-3 of the '069 patent, the metal-to-metal replacement includes a metallic (e.g. cobalt-chrome alloy) femoral prosthesis 22 and an acetabular prosthesis 40 also constructed of a metal material. Notably, FIG. 1 of the '069 patent shows that placement of the femoral prosthesis requires shaping of the femoral head 30 to fit a stem 24 and internal geometry of the femoral prosthesis. Shaping of the femoral head requires the use of various cutting and drilling tools. Accurate completion of such shaping procedures is aided by the accurate placement of a Steinman pin or guide wire 74 which guides the cutting and drilling tools. The '069 patent discloses what has become commonly known as femoral head resurfacing.

A clamp 62 is used to facilitate centering and placement of the guide wire, as shown in FIG. 9 of the '069 patent. The clamp includes a pair of jaws 64 that are supported by support member 68 and at pivot points 66 that allow pivotal rotation of the jaws with respect to the support member. Such rotation allows the jaws to engage the neck 32 of the femur 28. The jaws are advanced and retracted by rotation of a handle 70 which advances a threaded actuator 76 through the body and moves a camming surface 72 attached thereto. The camming surface, in turn, drives opening and closure of the jaws about the neck. After the clamp is secured, the pin or guide wire is inserted into, and advanced through, collinear guide openings defined in the handle and threaded actuator until hitting an entry point 78 on the femoral head 30. Advantageously, the ability of the clamp to engage and hold the guide openings in a fixed position relative to the femur promotes the accurate insertion of the guide wire or pin.

Despite the advantages of the clamp disclosed by the '069 patent, further improvements in the adjustability of positioning of pins and guide wires to improve the accurate placement of femoral prostheses are always desirable. It would be advantageous, therefore, to have a clamp and method with improved options to easily and accurately place a guide wire or pin which is subsequently used to guide femoral head resurfacing.

BRIEF SUMMARY OF THE INVENTION

The present invention addresses the above needs and achieves other advantages by providing a guide clamp for clamping a femur and guiding placement of a guide wire relative to the femur It is an object of the invention to provide a guide clamp capable of one-handed operation.

It is an object of the invention to provide a guide clamp that provides for the more accurate centering of guide pins in, for example, the femoral head.

These and other objects of the invention are achieved by a guide clamp for clamping of a femur having a head and a neck, and guiding placement of a guide wire relative to the femur, the guide clamp comprising: at least two clamping surfaces configured to move between an open position and a closed position, wherein the clamping surfaces are sufficiently spaced apart in the open position to allow insertion of the femur therebetween and wherein the clamping surfaces generally oppose each other and are sufficiently close together in the closed position to firmly hold the femur therebetween; a body supporting the clamping surfaces and configured to allow movement of the clamping surfaces relative to each other, the body defining a guide opening configured to receive and allow passage of the guide wire therethrough to the femur; and a biasing assembly configured to bias the clamping surfaces into the closed position about the femur wherein the clamping surfaces secure the body relative to the femur so that the guide wire is secured relative to the femur when extending through the guide opening defined by the body.

These and other objects of the invention are achieved by a guide clamp for clamping of a femur and guiding placement of a guide wire relative to the femur, the guide clamp comprising: at least two clamping surfaces configured to move between an open position and a closed position, wherein the clamping surfaces are sufficiently spaced apart in the open position to allow insertion of the femur therebetween and wherein the clamping surfaces generally oppose each other and are sufficiently close together in the closed position to firmly hold the femur therebetween; a body supporting the clamping surfaces and configured to allow movement of the clamping surfaces relative to each other, the body defining a guide opening configured to receive and allow passage of the guide wire therethrough to the femur; and an engagement member supported by the body and which is configured to extend therefrom into abutting contact with the head of the femur when the contact surfaces are in the closed position and the clamping surfaces secure the femur.

Furthermore, it is an object of the invention to provide a method of using the guide.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION OF THE INVENTION

The present invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout.

Figure 1:
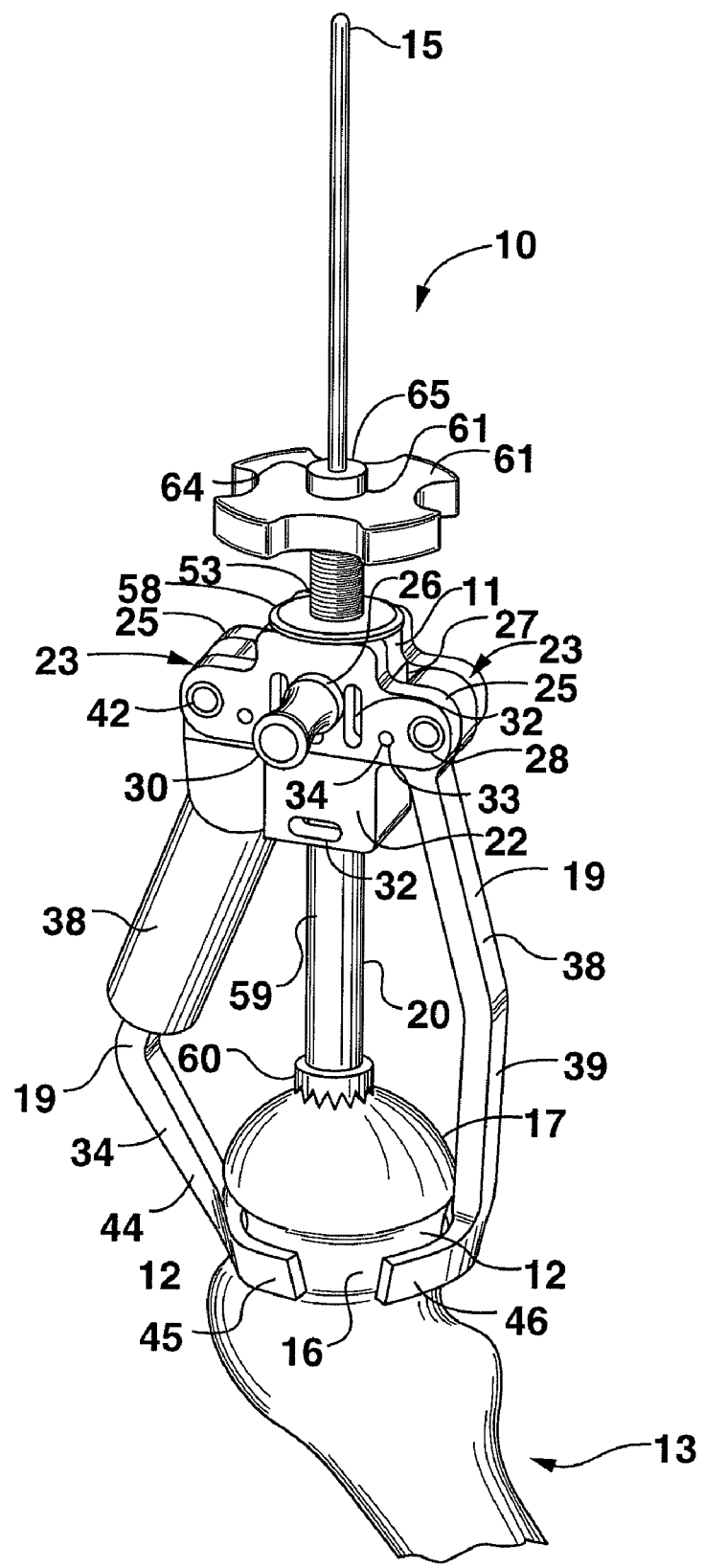
FIG. 1 is a perspective view of a guide clamp of one embodiment of the present invention secured to a femur.
Figure 1A:
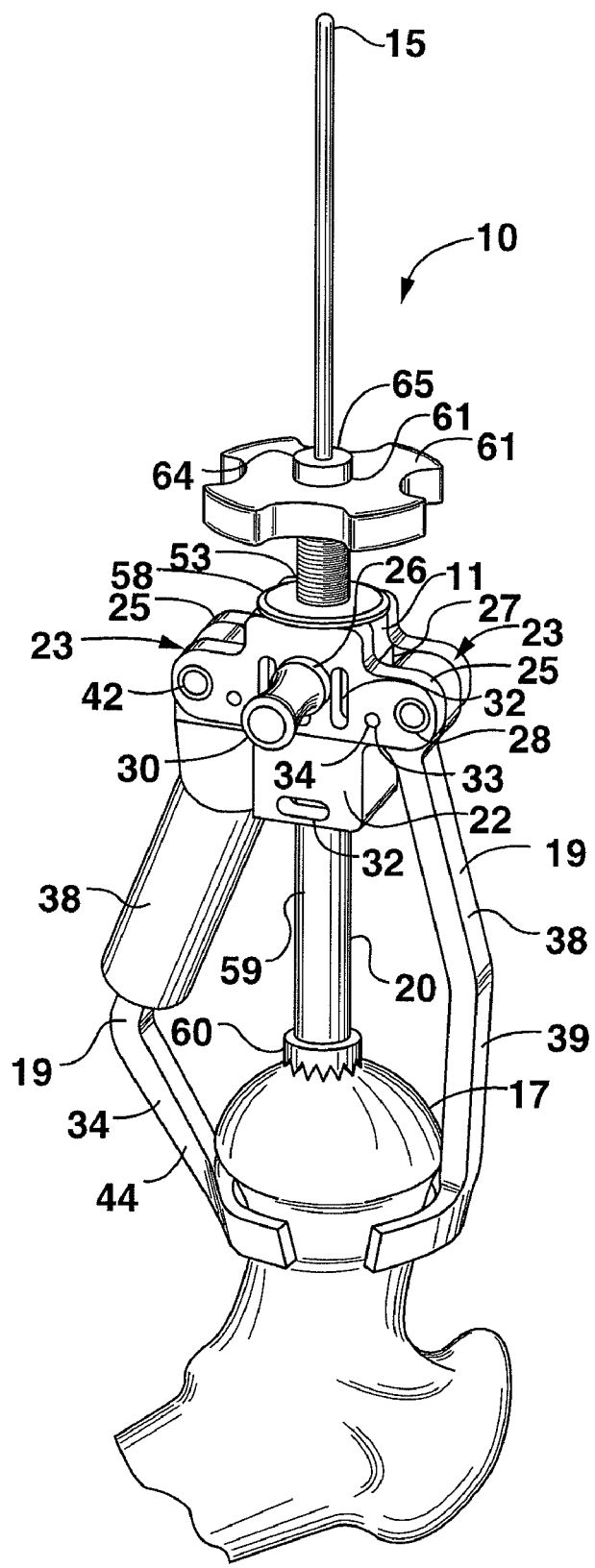
FIG. 1A is a perspective view of a guide clamp of one embodiment of the present invention secured in a preferred orientation on a femur.
Figure 2:
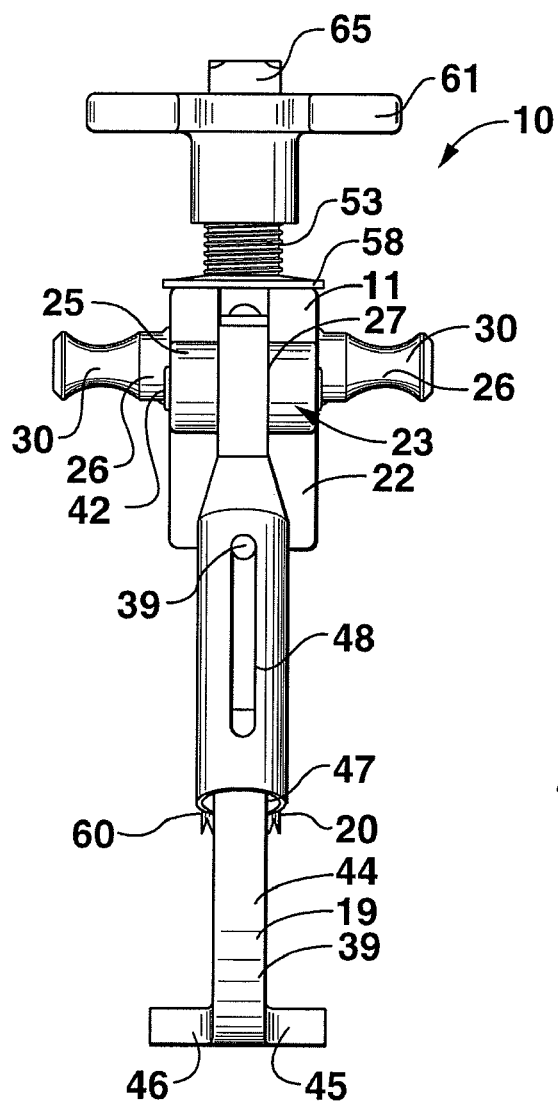
FIG. 2 is a side elevation view of the guide clamp of FIG. 1.
Figure 3:
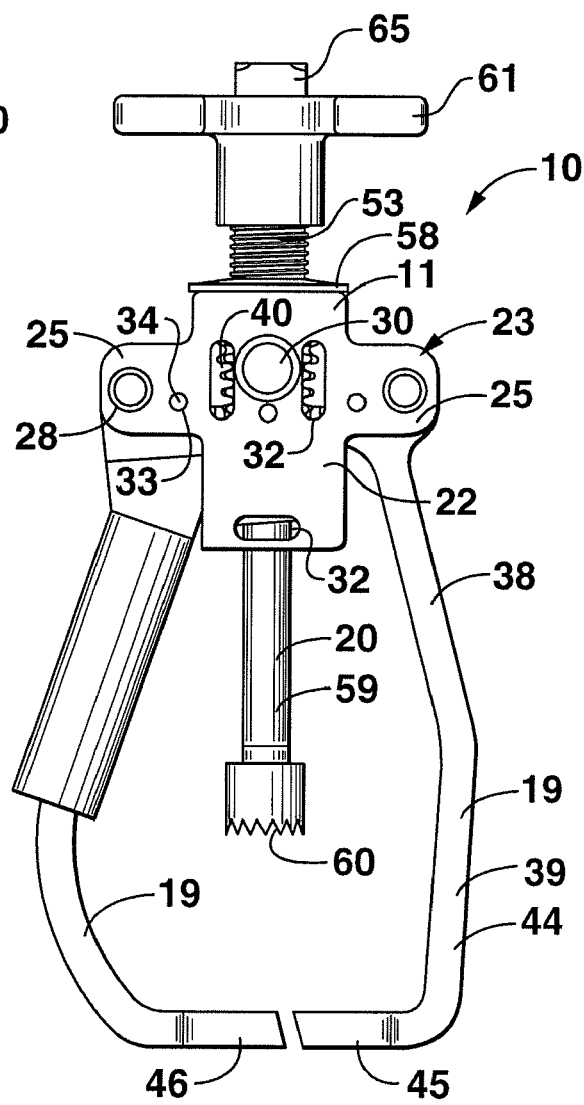
FIG. 3 is a front elevation view of the guide clamp of FIG. 1.

A guide clamp 10 of one embodiment of the present invention includes a body 11 movably supporting two or more clamping surfaces 12 that can be moved from an open (separated) position that allows insertion of a femur 13 (and more specifically the femoral head 17) therebetween and a closed position wherein the clamping surfaces are firmly secured about the femur (e.g., around a neck 16 of the femur), as shown in FIGS. 1-3. Defined in the body 11 is a guide opening 14 that allows passage of a primary guide shaft 59. In turn, the primary guide shaft 59 defines a guide opening 64 that allows direct passage of a Steinmann pin or guide wire 15 directly therethrough to intersect a head 17 of the femur 13. The term "guide opening" as used herein describes any opening that directly (e.g., guide opening 64), or indirectly (e.g., guide opening 14 which houses the guide shaft 59 defining directly guiding opening 64), supports the guide wire 15.

When firmly secured about the femur, the guide clamp 10 preferably aligns guide openings 14, 64 with the central axis of the femoral head 17 and the clamping surfaces grip the femur sufficiently tightly to allow steady guidance of the guide wire as its extends to the femur 13. Generally, the guide clamp 10 can further include one or more alternative or combined aspects of the invention, such as: the use of a biasing assembly 18 (FIG. 14) and/or use of an engagement member 20.

Referring in particular to FIG. 1, the femur of the patient is shown disassociated from the acetabular socket (not shown) and includes the femoral head 17 separated by the femoral neck 16 from the remaining portions of the femur 13. Generally, as is typical in most humans, the femoral head 17 has a semi-spherical shape that at its base is supported by the neck 16 which is roughly cylindrical with a narrowing diameter as it extends to its attachment to the rest of the femur 13. Although the guide clamp 10 of the present invention is preferably used to place the guide wire 15 in the femoral head 17, the guide clamp could also be used to place the guide wire in other parts of the femur, or even other bones, such as the tibia or humerus, where the guide wire needs to be centered along the axis of a ball and socket joint.

Anatomical terminology is used herein, and in particular the terms "proximal" and "distal," are used herein to refer to guide clamp 10 as if it were attached to the femur 13 in the anatomical position with a top of the guide clamp (with respect to its orientation in FIG. 1) being proximal and the bottom of the guide clamp extending distally to attach to the femoral neck 16. However, these directional references are used for clarity and convenience and it should be recognized that other orientations are also possible for the guide clamp 10 and still fall within the purview of the present invention.

Figure 4:
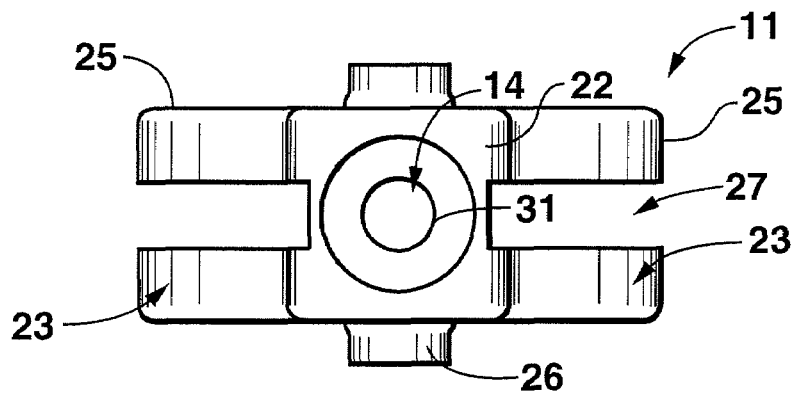
FIG. 4 is a plan view of a body of the guide clamp of FIG. 1.
Figure 5:
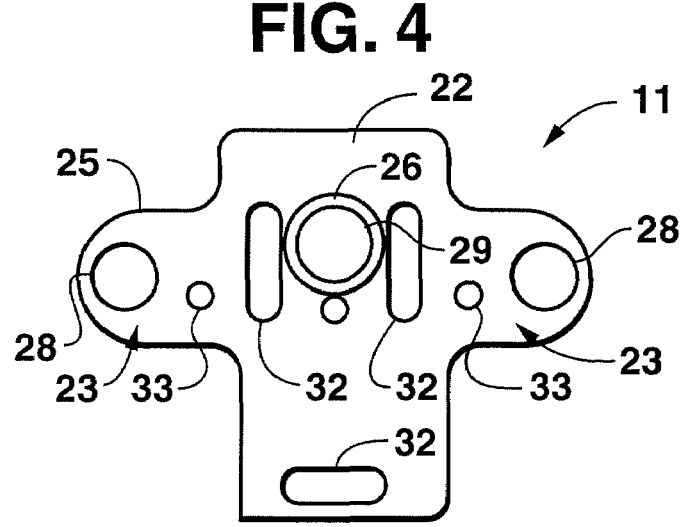
FIG. 5 is a side elevation view of a body of the guide clamp of FIG. 1.
Figure 6:
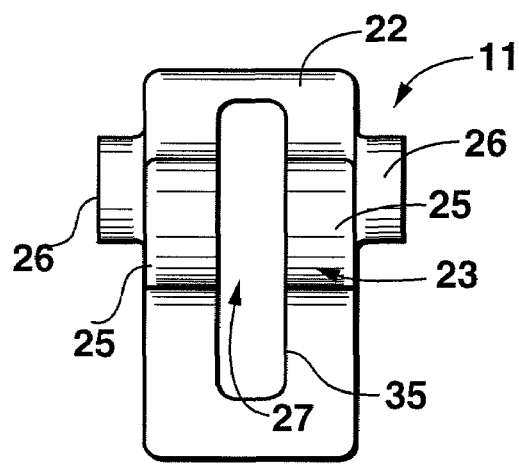
FIG. 6 is another side elevation view of a body of the guide clamp of FIG. 1.

The body 11 of the illustrated guide clamp 10 may be constructed of a unitary piece of material having a main portion 22, a pair of devises 23 and a pair of finger grip mounts 26, as shown in FIGS. 4-6. The devises 23 are spaced apart on opposite lateral sides of the main portion 22. Each of the devises 23 includes a pair of clevis members extending laterally from the lateral sides of the main portion 22.

The clevis members 25 of each pair are spaced from each other and define a clevis slot 27 therebetween. Each of the clevis members 25 defines a cylindrical opening 28. The cylindrical opening of each of the clevis members 25 is concentrically aligned with the cylindrical opening 28 of the adjacent one of the clevis members. This arrangement allows each adjacent pair of the cylindrical openings to receive one of a pair of arm shafts 42 so as to form a rotatable mount for supporting one of a pair of clamping arms 19 which, as described below, serve as supports for the clamping surfaces 12.

The finger grip mounts 26 are positioned on the remaining opposite sides of the main portion 22 (that the clevis members 25 are not on) and extend outwards from the main portion, as shown in FIG. 4. Each of the finger grip mounts 26 defines a threaded cylindrical opening 29 which is aligned with the threaded cylindrical opening defined by the other one of the finger grip mounts. The finger grip mounts 26 allow attachment of a pair of finger grips 30 on opposite sides of the main portion 22.

Defined by the main portion 22 are a plurality of openings, including the guide opening 14 (as shown in FIG. 4), three view ports 32, a pair of restraining pin mounts 33 (as shown in FIG. 5) and a pair of clamping arm guides 35 (as shown in FIG. 6). Two of the view ports 32 are spaced on opposite sides of the finger grip mounts 26 and one of the view ports is positioned at the distal end of the main portion. The restraining pin mounts 33 are positioned adjacent the devises 23 and are sized and shaped to receive restraining pins 34.

Figure 14:
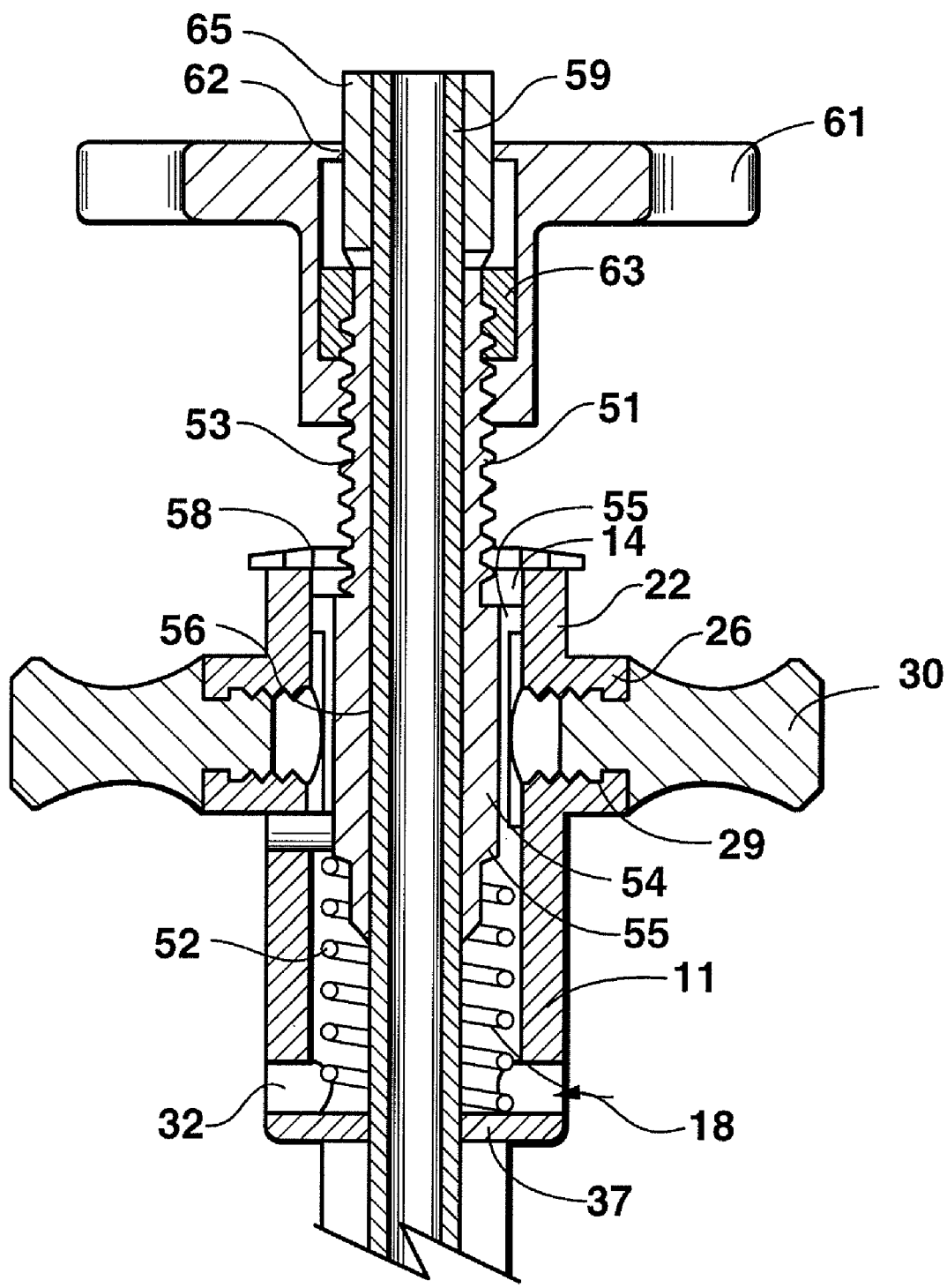
FIG. 14 is a cross-sectional view of the guide clamp of FIG. 1.

The guide opening 14, as shown best in FIG. 4, has a cylindrical shape and extends in the proximal-distal direction from a proximal end of the body 11 to a distal end of the body. The diameter of the body guide opening 14 is the same for most of its length with the exception of a stepped drop to about half its major diameter immediately adjacent the distal end of the body 11 which is due to an inwardly directed retaining flange 57 of the body, as shown in FIG. 14. The clamping arm guides 35 are elongated slots defined on opposite sides of the main portion 22 and are positioned between respective pairs of the clevis members 25 at the base of each clevis slot 27, as shown in FIG. 6. The clamping arm guides 35 are in communication with the distal portion of the guide opening 14 so as to allow passage therethrough of proximal ends of the clamping arms 19.

The term "body" as used herein should be construed broadly to include any structure, or combination of structures, that provide movable support for at least one of the clamping surfaces 12 and defines one or more openings (e.g., opening 14) through which the guide wire 15 can be extended. Movably supporting the clamping surfaces 12 refers to allowing, or facilitating movement in one or more degrees-of-freedom of at least one of the clamping surfaces so that they can be positioned relative to each other in the open and closed positions. For instance, the body could define track openings having cam shapes that allow combined translation and rotation of the clamping arms 19 for movement of the clamping surfaces 12 between the open and closed positions.

Figure 7:
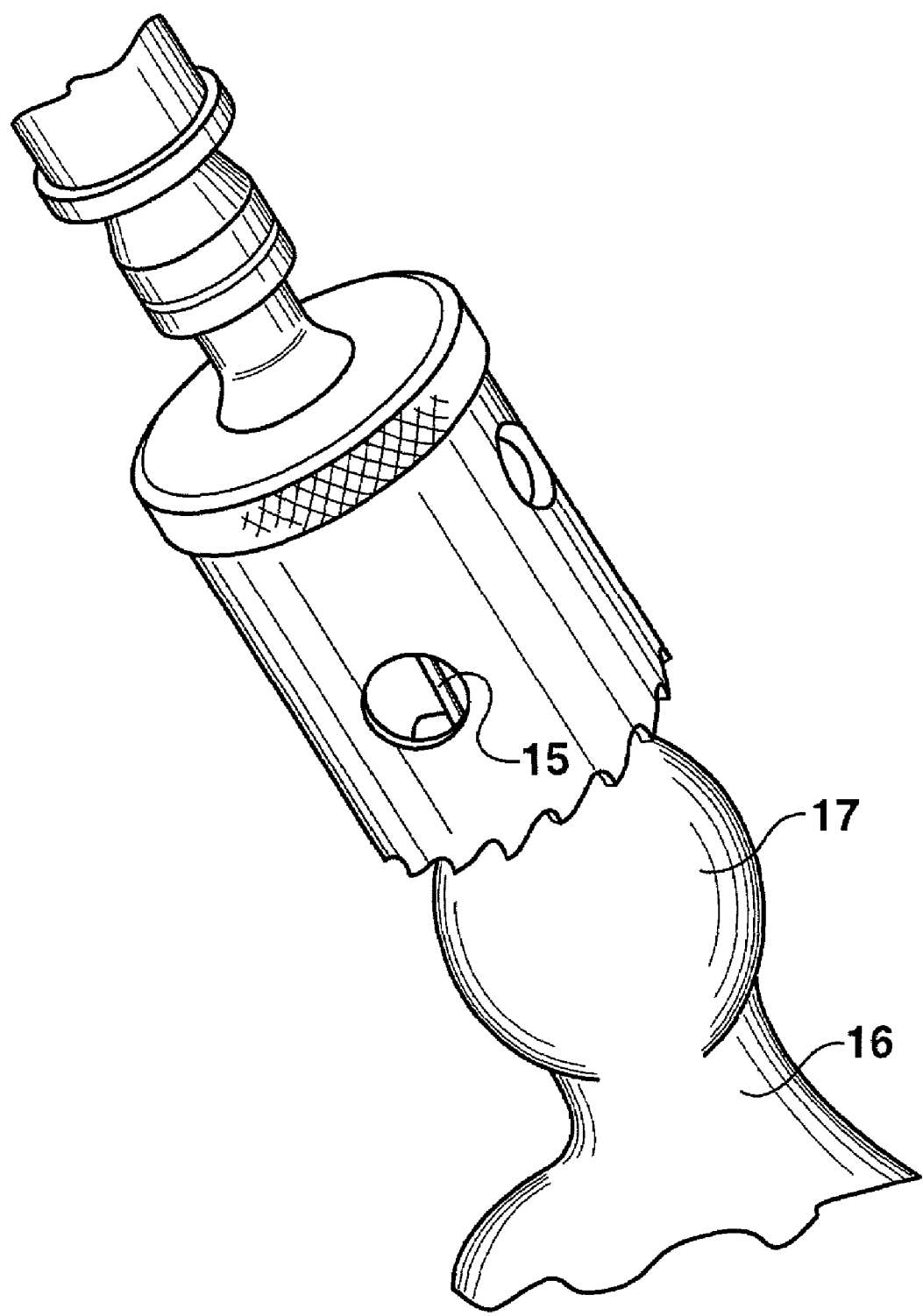
FIG. 7 is perspective view of a guide pin being used to guide resurfacing of a femoral head, said guide pin having been placed by the guide clamp of FIG. 1.

As another example, the body could define multiple guide openings 14, or differently shaped guide openings, and still fall within the purview of the present invention. Multiple guide openings could be used to directly or indirectly support multiple guide wires, or provide alternative position selections for the guide wires. Different sized and shaped guide openings can facilitate different sized and shaped guide wires. The terms "guide wire" and "guide pin" or "pin" are used interchangeably herein to denote a generally elongate, rigid member used as a fixed reference point for e.g. resurfacing of the femoral head 17, as shown in FIG. 7, or other portion of a patient's anatomy. Typically, that fixed reference point will be the central axis of the femoral head.

Figures 8, 9:
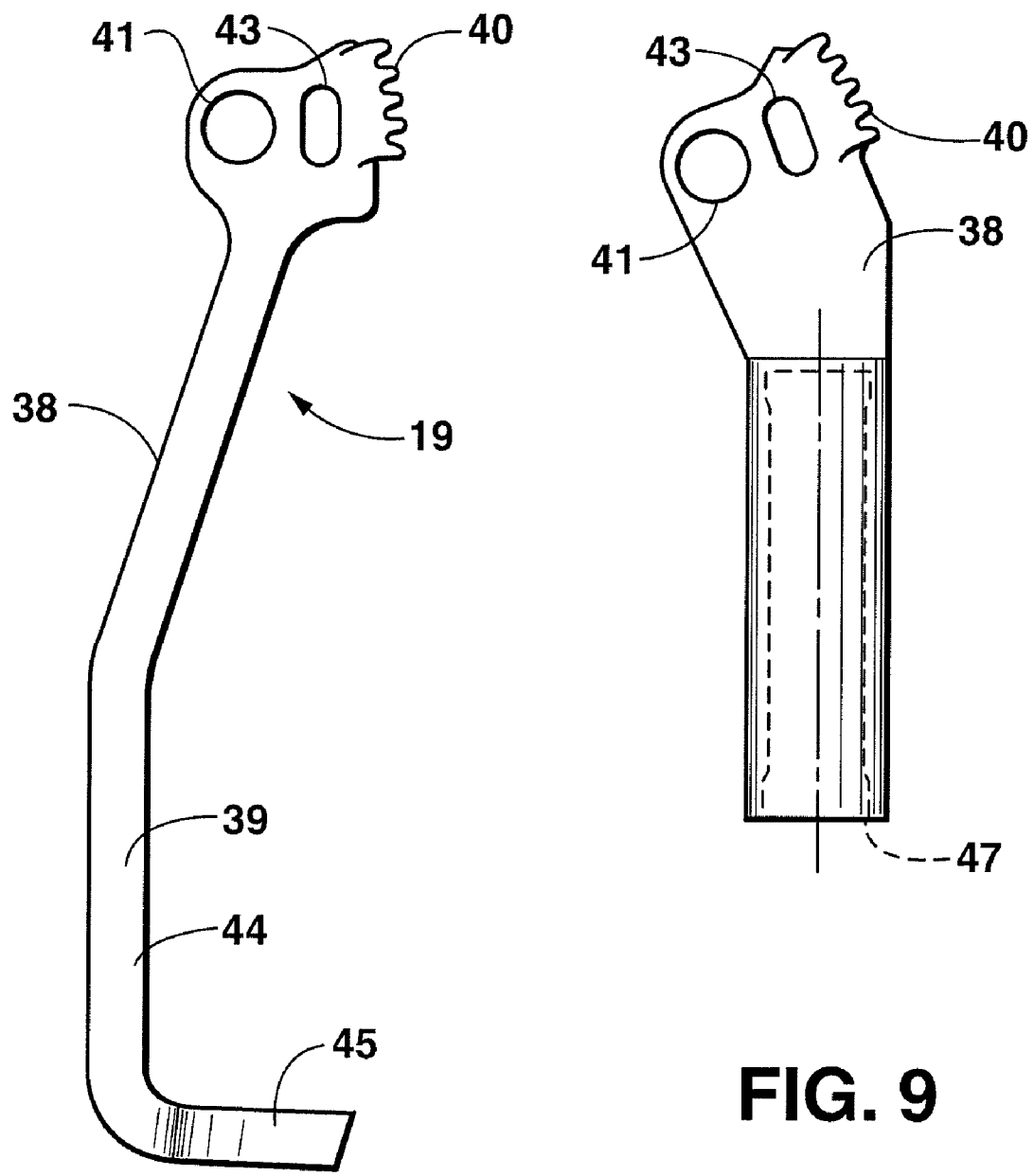
FIG. 8 is a side elevation view of a clamping arm of the guide clamp of FIG. 1.
FIG. 9 is a side elevation view of a proximal portion of another clamping arm of the guide clamp of FIG. 1.

Each of the clamping arms 19 includes a first, proximal portion 38 and a second, distal portion 39, as shown in FIGS. 1-3. The proximal portion 38 includes a plurality of pinion teeth 40 and defines a rotation shaft opening 41 and a restraining pin slot 43 positioned between the pinion teeth and the rotation shaft opening, as shown in FIGS. 8 and 9. The rotation shaft opening 41 is sized and shaped to receive a cylindrical arm shaft 42 which extends through the cylindrical opening 28 in each of a pair of adjacent clevis members 25 to rotatably support the clamping arm between the clevis members in the clevis slot 27, as shown in FIGS. 1-3.

Each of the restraining pins 34 similarly extends through the aligned pair of restraining pin mounts 33 and the restraining pin slot 43 in the proximal portion 38 of a respective one of the clamping arms 19. The restraining pin slot 43 allows sliding of the restraining pin therein while the clamping arm rotates about the arm shaft 42. However, the ends of the restraining pin slot 43 serve as end points for the rotation about the arm shaft 42.

Figure 10:
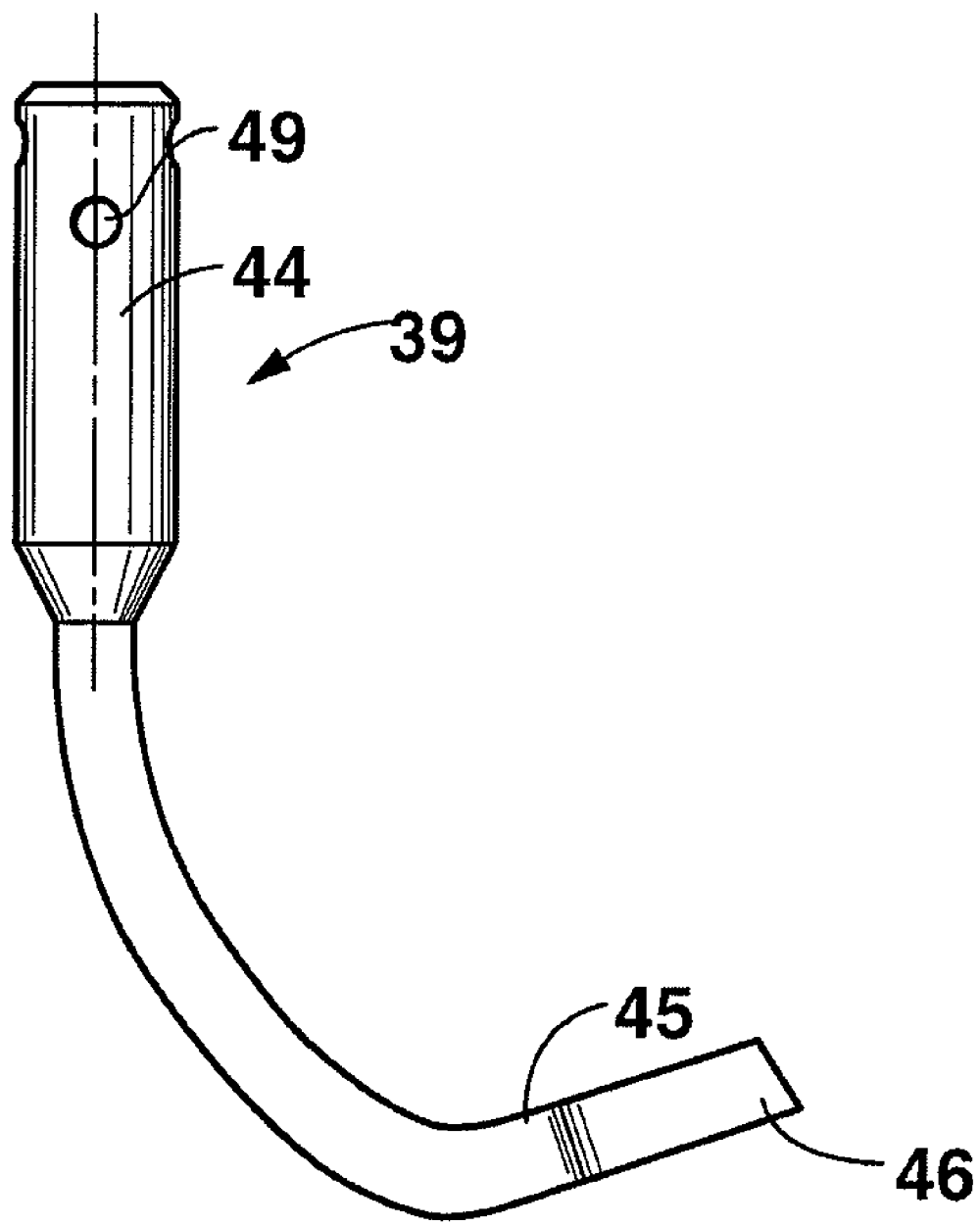
FIG. 10 is a side elevation view of a distal portion of the clamping arm of the guide clamp of FIG. 1.
Figure 11:
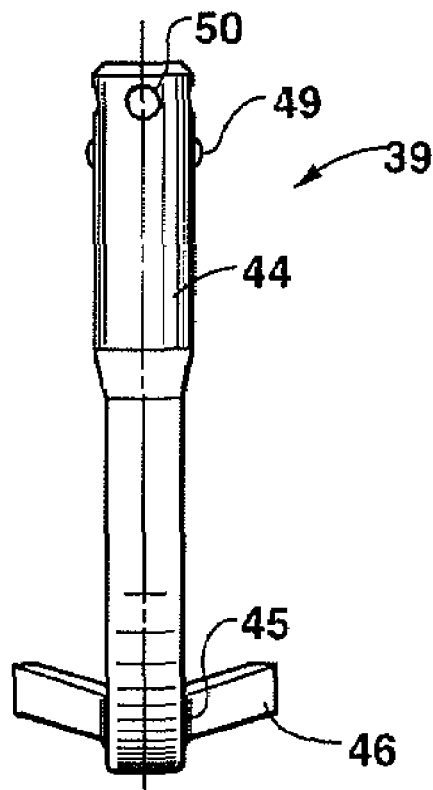
FIG. 11 is another side elevation view of the distal clamping arm portion of FIG. 10.
Figure 12:
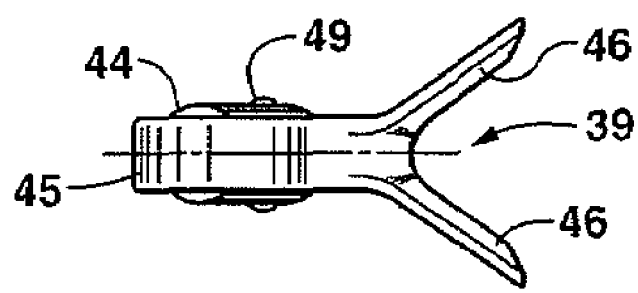
FIG. 12 is a plan view of the distal clamping arm portion of FIG. 10.

The distal portion 39 of each of the clamping arms 19 extends distally and towards the distal portion of the other one of the clamping arms 19 when in the closed position, as shown in FIGS. 8 and 10. In particular, the distal portion 39 includes a distally directed first sub-portion 44 and second sub-portion 45 extending therefrom at a generally right angle thereto in the direction of the other one of the clamping arms 19. As shown in FIGS. 11 and 12, the second sub-portion 45 bifurcates into a pair of prongs 46 defining the respective one of the clamping surfaces 12 which abuts the femoral neck 16 in the closed position.

As shown in FIG. 3, each of the clamping surfaces 12A, 12B are preferably sloped to form an oblique angle relative to the primary guide shaft 59, and more particularly to the axis of the guide opening 64 that passes through the primary guide shaft 59. The oblique angle is selected such that the clamping surfaces 12A, 12B orient the guide opening 64 slightly superior to the neutral axis of the femoral neck. This orientation causes the guide pin to enter the femoral head at a more vertical orientation than that of the natural neck. In turn, this allows the stem of a femoral head prosthesis to be implanted in a more vertical orientation, which distributes load more vertically and results in improved performance of the prosthesis. The axis of the femoral head prosthesis is preferably oriented about 5 degrees above the natural axis of the femoral neck. In order to achieve this orientation, the clamping surfaces 12A, 12B preferably have a slope of about five degrees relative to the axis of the guide opening 64.

Figure 13:
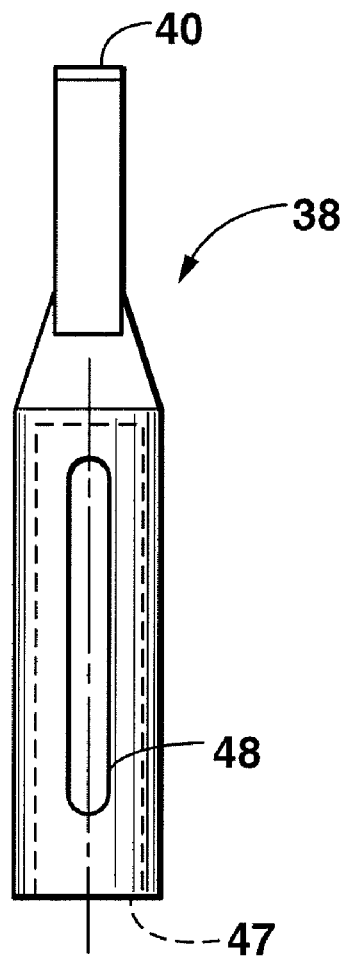
FIG. 13 is another side elevation view of the proximal portion of FIG. 9.

One of the clamping arms 19 has the optional feature of being adjustable independent of the coordinated movement of the pair of arms by the biasing assembly 18. In this embodiment, the adjustable one of the clamping arms 19 is separated into its proximal and distal portions, 38 and 39, respectively. The proximal portion has a widened distal sub-portion that defines an elongate opening 47 having a cylindrical shape that is open at the end opposite the pinion teeth 40, as shown in FIG. 13. Defined in the widened distal sub-portion is an elongate slot 48 that extends a majority of the length of the elongate opening 47 and is in communication therewith.

The first sub-portion 44 of the distal portion 39 of the adjustable one of the clamping arms 19 has its own widened cross-section and a cylindrical shape configured to be slidably mounted within the elongate opening 47 of the of the proximal portion 38, as shown in FIG. 2. The first sub-portion 44 also includes a pair of rounded, retaining protuberances 49 extending from opposite sides of the widened first sub-portion 44. These protuberances 49 extend between the walls of the proximal portion 38 within the elongate opening 47, so as to steady the distal portion 39 within the proximal portion 38, but still allow sliding motion therebetween. Optionally, the protuberances 49 may be outwardly biased (e.g., "ball and spring" members), but capable of being pressed against their bias into openings defined in the first sub-portion 44 under pressure. Use of ball and spring type members obviates the need to closely tolerance the size of the elongate opening 47 and the first portion 44.

Relative sliding of the proximal and distal portions, 38 and 39, of the adjustable one of the clamping arms 19 is restrained using a pin 50 that is sized to be slidably retained in the elongate slot 48 defined by the proximal portion 38. In this manner, the range of sliding of the two portions 38, 39 is restrained and the two portions do not disassociate from each other at the end of their sliding range.

Advantageously, the sliding adjustability of the portions of the adjustable one of the clamping arms 19 allows the angle of the clamping surfaces 12 to be changed relative to each other. Changing of the relative angle of the clamping surfaces changes the orientation of the guide opening 14, and hence the orientation of the guide opening 64, with respect to the femur 13 which aids the surgeon in optimizing positioning of the femoral head prosthesis. It should be noted that adjustability may be achieved using other configurations. For instance, a rotatable hinge member could be employed between the two portions 38, 39, or some type of multi-bar linkage. However, the illustrated embodiment has the advantage of an easily controlled adjustability due to the limitation of motion in a single sliding direction having fixed endpoints.

The biasing assembly 18 of the present invention provides biasing force to the clamping arms 19 so as to urge the clamping surfaces 12 together into the closed position abutting the femoral neck 16. The biasing assembly 18 may also coordinate movement of the two clamping arms 19 so that they move between the open and closed positions simultaneously via one-handed operation.

Figure 15:
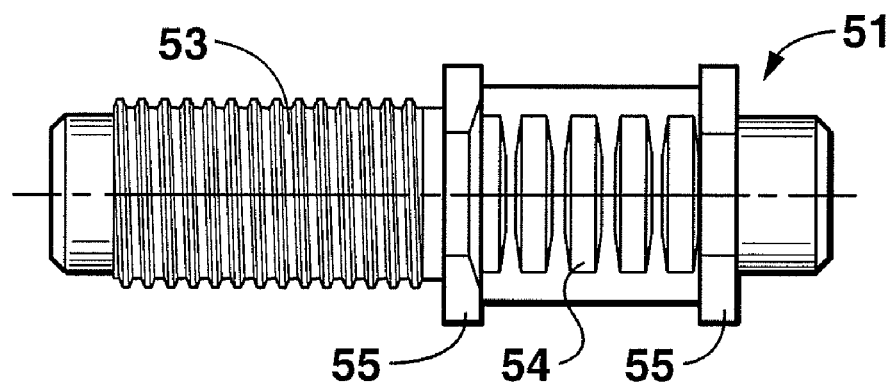
FIG. 15 is a side elevation view of a rack member of the guide clamp of FIG. 1.

In the illustrated embodiment, the biasing assembly is partially housed within the guide opening 14 of the body 11 and includes a rack member 51 and a coil spring 52, as shown in FIG. 14. The rack member 51 includes a threaded portion 53 that extends out of the body 11 and a portion bearing a plurality of rack teeth ("toothed portion") 54 that extends within the guide opening 14 of the body 11, as shown in FIG. 15. In addition, the rack member 51 defines its own guide opening 56 extending its entire axial length for allowing passage of the engagement member 20. The toothed portion is flanked by an opposing pair of flanges 55 and the teeth thereon extend outwards from a central axis of the rack member 51 and are adjacently positioned to extend between the pair of flanges. The threaded portion 53 extends from a side of one of the flanges 55 opposite the toothed portion 54 and includes threads extending around the outside of a cylindrical shaft.

When positioned within the guide opening 14 of the body 11, the coil spring 52 is positioned between the retaining flange 57 of the body 11 which narrows the body guide opening 14 and the distal one of the flanges 55 of the rack member 51. The rack member 51 is positioned adjacent the coil spring 52 at its distal end, a portion of which extends into the coil spring, and adjacent a retaining cap 58 at its opposite end, as shown in FIG. 14.

Positioning of the coil spring 52 at the distal end of the rack member 51 causes it to exert an upward bias onto the distal one of the flanges 55. This upward bias causes the toothed portion 54 to move upwards against the pinion teeth 40 of both of the clamping arms 19 which extend through the clamping arm guides 35 to mesh with the toothed portion. In turn, this upward bias causes coordinated movement distally and inwardly (due to rotation about the arm shaft 42) toward the femoral neck 16 of the clamping surfaces 12 at the opposite ends of the clamping arms 19 from the pinion teeth.

The retaining cap 58 is affixed to the body 11 and extends within the proximal end of the guide opening 14 of the body 11 to abut the proximal one of the flanges 55 of the rack member 51 when the clamping arms 19 are in the closed position, as shown in FIG. 1. In addition, the retaining cap 58 defines a central opening that is in communication with the guide opening 14 of the body 11 when secured to the body allowing passage therethrough of the engagement member 20.

Together, the retaining flange 57 and the retaining cap 58 hold the biasing assembly 18 within the guide opening 14 of the body 11 and provide a limit for the movement of the rack member 51, which in turn limits motion of the clamping arms 19. Further limitation of the motion of the biasing assembly 18 is achieved by tightening the finger grips 30 in the threaded openings 29 of the finger grip mounts 29 so that the ends of the finger grips abut the sides of the rack member 51. This also allows the user of the guide clamp 10 to lock the clamping arms 19 in place once the femoral neck 16 has been gripped by the clamping surfaces 12.

Figure 17:
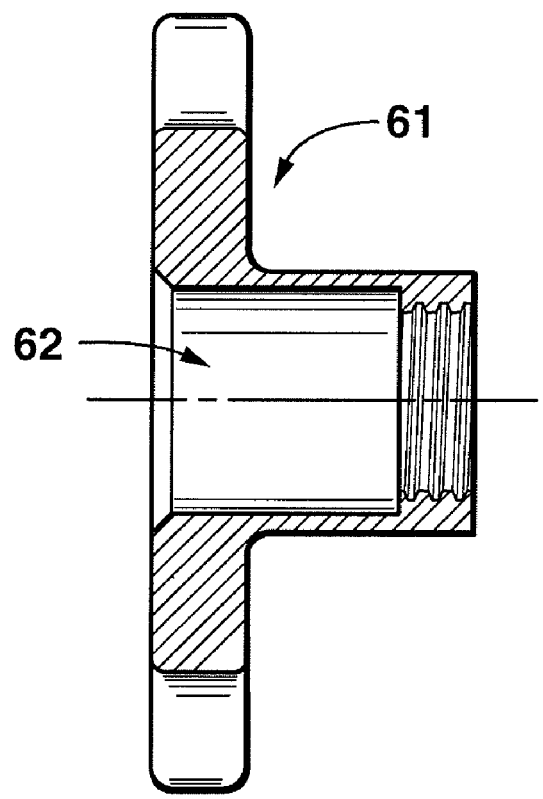
FIG. 17 is a cross-sectional view of a locking knob of the guide clamp of FIG. 1.

Additional limitation in the movement of the biasing assembly 18 can be achieved through use of a locking knob 61 that includes a central, threaded opening 62, as shown in FIGS. 14 and 17. The central, threaded opening of the locking knob 61 allows it to be advanced along the threaded portion 53 of the rack member 51 until it abuts the retaining cap 58 positioned on the body 11. If the proximal one of the flanges 55 on the rack member 51 is abutting the opposite side of the retaining cap 58, the position of the locking knob 61 will lock biasing assembly 18 into its abutting position against the retaining cap, thereby locking the clamping arms 19 and clamping surfaces 12 into the closed position.

Figure 16:
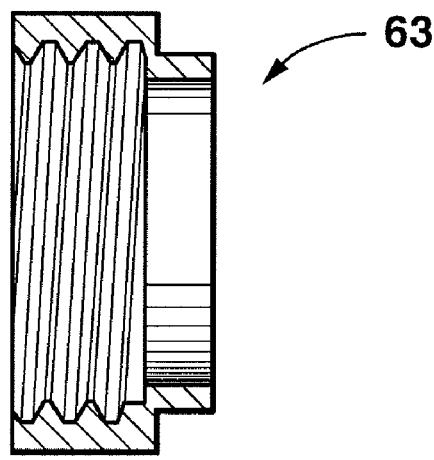
FIG. 16 is a cross-sectional view of a knob retaining cap of the guide clamp of FIG. 1.

Alternatively, advancement of the locking knob 61 short of co-abutment of the retaining cap 58 with the proximal one of the flanges 55 further reduces the range of motion of the rack member 51 in the distal direction. This effectively limits the proximal and outwards range of motion of the clamping arms 19 and the space between the clamping surfaces 12 when in the open position. Proximal movement of the locking knob 61 along the threaded portion 53 of the rack member 51 is restrained using a knob retaining cap 63, as shown in FIGS. 14 and 16. The knob retaining cap has a threaded opening to allow it to be secured on the most proximal end of the threaded portion 53 of the rack member 51.

It should be noted that the biasing assembly 18 can include various different components as long as it biases the clamping surfaces 12 into the closed position about the femoral neck 16 and preferably also coordinates movement of the clamping surfaces. For instance, the biasing assembly could include leaf or coil springs incorporated in the clamping arms 19 to urge the clamping surfaces together 12. Notably, in such a configuration the biasing assembly is not necessarily contained within the body 11 of the guide clamp 10. However, the biasing assembly 18 of the illustrated embodiment being at least partially contained within the guide opening 14 of the body 11 has the advantages of limiting movement as described above.

Figure 18:
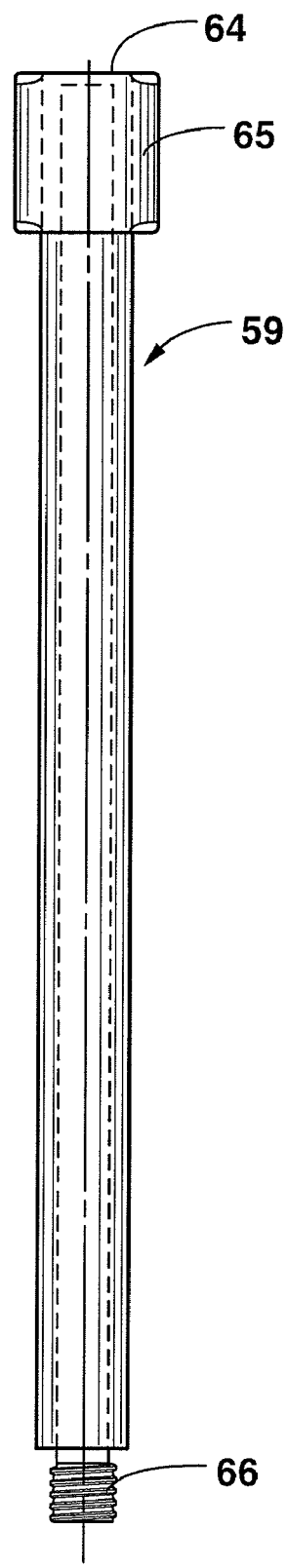
FIG. 18 is a side elevation view of a primary guide shaft of the guide clamp of FIG. 1.

In another aspect, the guide clamp 10 of the present invention may include the engagement member 20. The engagement member includes the primary guide shaft 59 and a textured tip 60. As shown in FIG. 18, the primary guide shaft 59 of the illustrated embodiment is an elongate, cylindrical shaft defining the guide opening 64 extending its entire length. Unlike the previously described guide openings, the guide opening 64 of the primary guide shaft 59 is in direct contact with the guide wire 15 as it extends through the guide clamp 10. The primary guide shaft 59 includes a retaining ring 65 fixed to its proximal end and a threaded portion 66 at its distal end having a reduced diameter.

Figure 19:
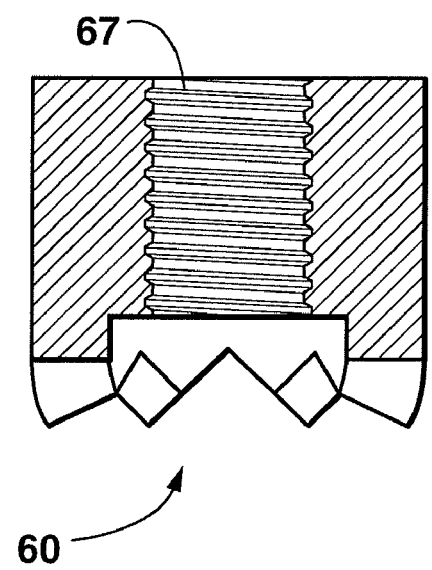
FIG. 19 is a side elevation view of a textured tip of the guide clamp of FIG. 1.

The textured tip 60 of the illustrated embodiment also has a cylindrical shape and the distal end of the textured tip 60 has a plurality of serrations that provide a textured gripping surface for abutting the femoral head 17, as shown in FIG. 1. In addition, the textured tip 60 defines a threaded opening 67 (as shown in FIG. 19) that is sized to mate with the threaded portion 66 at the distal end of the primary guide shaft 59, allowing the textured tip to be secured thereto. The term "textured" as used herein denotes any type of surface or pattern that facilitates a non-slip abutment with the femoral head 17, such as crenellations, cross-hatching or the illustrated serrations. Non-slip abutment with the femoral head is preferable so as to assure a proper and more accurate path for the guide wire along the selected reference line/point.

Threaded attachment facilitates assembly of the guide clamp 10 by allowing the primary guide shaft 64 to be inserted through the opening of the retaining cap 58, the guide opening 56 of the rack member 51, the coil spring 52 and the opening in the retaining flange 57 of the body 11 until its distal end extends out of the body. The threaded opening 67 of the textured tip 60 is then secured on the threaded portion 66 of the primary guide shaft 59.

The various openings through which the primary guide shaft 59 extends are sized to allow sliding of the engagement member 20 so that it can be advanced and retracted from abutting contact with the femoral head 17. Advancement and retraction is limited by the retaining ring 65 at the proximal end of the engagement member 20 and the textured tip 60 at the distal end of the engagement member. While it is possible to provide a means for locking the engagement member adjacent the femoral head, such will typically not be necessary. The friction forces between the engagement member and the guide shaft and the non-slip abutment are typically enough to prevent unwanted movement of the engagement member.

It should be noted that the engagement member 20 of the present invention need not be limited to the illustrated embodiment and can include any member, or combination of members (such as an arm that swings distally to contact the femoral head 17), that are capable of providing a moveable third surface for engagement with the femur 13 in addition the to clamping surfaces 12. Preferably, the engagement member 20 also further provides an extended guide opening that is capable of guiding insertion of the guide wire 15 right up to the surface of the femoral head 17.

Having described the structure of guide clamp 10, we will now describe its use.

During use, the user grasps body 11 in between, e.g., the user's first and middle finger, with the first and middle finger gripping finger grips 26 and locking knob 61 of the guide clamp 10 to be manipulated by the thumb of the same hand. The locking knob 61 is then pushed into the body 11 by the thumb, which moves the rack member 51 against the bias of the coil spring 52. The teeth of the toothed portion 54 cause the pinion teeth 40 at the proximal portion 38 of the clamping arms 19 to rotate distally about the arm shafts 42, causing the distal portion 39 of the clamping arms, and the clamping surfaces 12 supported thereby, to move proximally and outwardly away from each other into an open position. At this point, the femur 13, and in particular the femoral neck 16, is inserted in between the pair of clamping surfaces 12.

Once the femoral neck 16 has been positioned the locking knob 61 is released allowing the toothed portion 54 to be urged proximally by the coil spring 52. Such urging causes the toothed portion 54 and pinion teeth 40 to interact and rotate the proximal portion 38 of each of the clamping arms 19 proximally about the arm shafts 42. In turn, the distal portion 39 of the clamping arms 19, and the clamping surfaces 12 supported thereby, rotate about the arm shafts 42 distally and towards each other to close about the femoral neck 16. Once in the closed position, the locking knob 61 can be advanced on the threaded portion 53 until it abuts the retaining cap 58 and holds the proximal one of the flanges 55 against the other side of the retaining cap. This effectively locks the guiding clamp 10 into position on the femur 13. Thus, what was originally a two-handed operation has now been reduced to a one-handed operation.

Adjustments to the angle of the guide opening 64 of the primary guide shaft 59 with respect to the femoral head 17 can be made by adjusting the adjustable one of the clamping arms 19. For instance, the distal portion 39 of the clamping arm can be slid within the elongate opening 47 defined by the proximal portion 38 until a desired change in angle is achieved.

Once the clamping surfaces 12 have been secured in the closed position, the primary guide shaft 59 of the engagement member 20 is advanced within the guide opening 56 of the rack member 51, and other openings, until the textured tip 60 abuts the femoral head 17. In this manner, the guide opening 64 of the primary guide shaft 59 extends right up to the surface of the femoral head 17. The guide wire 15 is then inserted into guide opening 64 defined at the retaining ring 65 of the engagement member, and is advanced through the rest of the guide opening 64 of the primary guide shaft 59 until it intersects the femoral head 17. The guide wire 15 is then driven into the femoral head 17 using a hammer, drill or other device known in the art.

Once the pin has been secured, the guide clamp 10 is removed by loosening the locking knob 61 and repeating the steps described above for moving the clamping surfaces 12 to the open position. After removal of the guide clamp 10, the guide wire 15 is used as a guide for cutting the femoral head 17 using a cannulated drill and bit, as shown in FIG. 7.

The present invention has many advantages. For example, coordinated, biased closing movement of the clamping surfaces 12 using the biasing assembly 18 allowing for one-handed operation. Such coordinated, biased closing movement ensures that the clamping arms 19 and their clamping surfaces 12 center the femoral neck 16 between them for proper alignment of the various guide openings with the femoral head 17. The adjustability of one, or more, of the clamping arms 19 allows for modifications of the angle at which the various guide openings, and hence the angle of the guide wire 15, will be positioned with respect to the femoral head 17. The engagement member 20 bridges the gap between the body 11 of the guiding clamp 10 and the femoral head 17 by providing additional guide opening length up to the femoral head. This improves the accuracy of placement of the guide wire 15. In addition, the textured tip 60 of the engagement member increases the security of the grip that the guiding clamp 10 has on the femur 13.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A guide clamp for clamping of a femur having a head and a neck, and guiding placement of a guide wire relative to the femur, said guide clamp comprising:
   a pair of clamping arms, wherein each of said clamping arms includes a plurality of pinion teeth and a clamping surface so as to be configured to move between an open position and a closed position, wherein said clamping surfaces are sufficiently spaced apart in the open position to allow insertion of the femur therebetween and wherein said clamping surfaces generally oppose each other and are sufficiently close together in the closed position to firmly hold the femur therebetween, a body rotatably supporting both of said clamping arms and configured to allow movement of the clamping surfaces relative to each other, said body defining a first guide opening configured to receive and allow passage of a guide shaft having a distal end, the guide shaft defining a second guide opening sized to receive and directly contact the guide wire slidingly therethrough to the femur when said distal end engages the femur; and a biasing assembly partially disposed within the body, the biasing assembly including a spring and a translation member, the spring disposed distally with the body with respect to the translation member and configured to linearly bias the translation member in a proximal direction with respect to said body thereby biasing the clamping arms in a distal direction with respect to the body, said translation member defining said first guide opening and including a plurality of rack teeth configured to engage said pinion teeth of both of said clamping arms so that movement of said translation member causes rotation of said clamping arms and relative movement of said clamping surfaces into the closed position about the femur wherein the clamping surfaces secure the body relative to the femur so that the guide wire is secured relative to the femur when extending through said guide shaft.

2. A guide clamp of claim 1, wherein the spring is configured to bias both of the clamping arms and coordinate movement of the clamping surfaces between the open and closed positions.

3. A guide clamp of claim 1 wherein the spring is a coil spring including a first end abutting the body and a second end abutting the translation member.

4. A guide clamp of claim 3, wherein the coil spring extends about the translation member.

5. A guide clamp of claim 1, further comprising an engagement member extending from said distal end of said guide shaft so as to be in abutting contact with the head of the femur when secured between the clamping surfaces.

6. A guide clamp of claim 5, wherein the engagement member defines a guide opening aligned with the first guide opening defined in the body and allowing passage of the guide wire through both of the guide openings to the head of the femur.

7. A guide clamp of claim 6, wherein the engagement member is movably supported by said guide shaft allowing the engagement member to be retracted from, and extended into, abutting contact with the head of the femur.

8. A guide clamp of claim 7, wherein said guide shaft is configured to slidably support said guide wire along the axis of said first guide opening defined by the body allowing the guide wire to be retracted from, and extended into, abutting contact with the head of the femur.

9. A guide clamp of claim 8, wherein the engagement member includes a textured femur-adjacent end.

10. A guide clamp of claim 9, wherein the textured femur-adjacent end includes serrations.

11. A guide clamp of claim 1, wherein each of the clamping surfaces are sloped to form an oblique angle relative to the guide opening to thereby position said guide opening at an offset angle relative to a natural axis of a femur, the offset angle being more vertical than that of the natural axis of the femur.

12. A guide clamp of claim 11, wherein the slope of the clamping surfaces is about 5 degrees.

13. The guide claim of claim 1, wherein one of the clamping arms includes an adjustable portion configured to adjust a relative angle of the clamping surfaces.

\* \* \* \* \*